US00PP20800P2

(12) United States Plant Patent
Verschoor

(10) Patent No.: US PP20,800 P2
(45) Date of Patent: Mar. 2, 2010

(54) ***PHLOX* PLANT NAMED 'TEQUILA SUNRISE'**

(50) Latin Name: *Phlox paniculata*
Varietal Denomination: Tequila Sunrise

(76) Inventor: Jan Verschoor, Mercelisvaartpad 17, Haarlem (NL) 2015 CS ( * ) Notice: Subject to any disclaimer, the term of this patent is extended or adjusted under 35 U.S.C. 154(b) by 0 days.

(21) Appl. No.: 12/316,134

(22) Filed: Dec. 10, 2008

(51) Int. Cl.
*A01H 5/00* (2006.01)

(52) U.S. Cl. ..... Plt./320

(58) Field of Classification Search ..... Plt./320
See application file for complete search history.

*Primary Examiner*—Annette H Para
(74) *Attorney, Agent, or Firm*—Audrey Charles

(57) ABSTRACT

A new and distinct cultivar of *Phlox* plant named 'Tequila Sunrise', particularly distinguished by salmon and pink-colored flowers, compact habit, healthy foliage, and good mildew resistance, is disclosed.

2 Drawing Sheets

Latin name of genus and species of plant claimed: *Phlox paniculata.*

Variety denomination: 'Tequila Sunrise'.

BACKGROUND OF THE INVENTION

The present invention relates to a new and distinct cultivar of *Phlox* plant botanically known as *Phlox paniculata* and hereinafter referred to by the cultivar name 'Tequila Sunrise'. The new cultivar originated from an open pollination in 2006 in a nursery location in Haarlem, The Netherlands between unknown male and female *Phlox paniculata* plants.

The new cultivar was selected from the results of the open pollination in 2007 in Haarlem, The Netherlands. Asexual reproduction of the new *Phlox* by vegetative cuttings in a controlled environment in Haarlem, The Netherlands since the summer of 2007, has shown that the unique features of the *Phlox* are stable and reproduced true to type in successive generations.

SUMMARY OF THE INVENTION

The following are the most outstanding and distinguishing characteristics of this new cultivar when grown under normal horticultural practices in Haarlem, The Netherlands:

1. Salmon and pink-colored flowers;
2. Compact habit;
3. Healthy foliage; and
4. Good mildew resistance.

Of the many commercially available *Phlox* cultivars, the most similar in comparison to the new cultivar is 'Windsor', not patented. However, in side by side comparisons in Haarlem, The Netherlands, plants of the new cultivar 'Tequila Sunrise' differ from plants of 'Windsor' by having healthier foliage, thicker stems, and a sturdier, more compact plant habit. Additionally, 'Tequila Sunrise' flowers more evenly with flowers that have a richer color than those of 'Windsor'.

In addition, plants of the new cultivar 'Tequila Sunrise' are similar to 'Strawberry Daiquiri', co-pending U.S. Plant Patent Application. However, in side by side comparisons in Haarlem, The Netherlands, plants of the new cultivar 'Tequila Sunrise' differ from plants of 'Strawberry Daiquiri' in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Tequila Sunrise'. The plant was grown for approximately 1 year in a 1.5-liter container in Haarlem, The Netherlands in an outdoor nursery location.

The photograph on the first sheet is a side view of the overall growth and habit of 'Tequila Sunrise'.

The photograph on the top of the second sheet is a close-up view of the inflorescence of 'Tequila Sunrise'.

The photograph on the bottom of the second sheet is a close-up view of the foliage of 'Tequila Sunrise'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The data which define these characteristics were collected from asexual reproductions carried out in Haarlem, The Netherlands. The plant history was taken in August on 1-year-old plants in 1.5 liter containers which were planted and grown outdoors in daytime temperatures between 14° C. and 32° C. and nighttime temperatures between 5° C. and 15° C. No pinching, growth retardants or photoperiodic treatments were used. Observations were made when the plants were in natural daylight conditions.

Botanical classification: *Phlox paniculata* cultivar 'Tequila Sunrise'.

Parentage:

*Female parent.*—Unknown *Phlox paniculata.*

*Male parent.*—Unknown *Phlox paniculata.*

Plant description:

*Type.*—Herbaceous perennial. Overall shape: Broad inverted triangle. High temperature tolerance: Tolerant to at least 35° C. Low temperature tolerance: Hardy to at least USDA Zone 4.

*Commercial crop time.*—Approximately 25 weeks from rooted cutting to finish in a 1.5 liter container.

*Growth habit and general appearance.*—Upright, moderately vigorous.

*Size.*—Height from soil level to top of plant plane: Approximately 50.8 cm. Width: Approximately 56.6 cm. Rate of growth: In spring, approximately 10 cm per month.

*Branching habit.*—Moderate basal branching; pinching will improve basal branching; flowering stems grow from base. Quantity of branches per plant: Approximately 18 flowering stems.

*Stem.*—Shape: Rounded. Strength: Strong. Aspect: Erect. Length to base of inflorescence: Approximately 34.9 cm. Diameter: Approximately 3.5 mm. Length of central internode: Approximately 3.7 cm. Texture: Glabrous, slightly glossy. Color of young and mature stems: 200B flushed with 146B toward apex.

Foliage description:

*General description.*—Quantity of leaves per stem: Approximately 18. Form: Simple. Arrangement: Opposite. Durability to stress: High.

*Leaves.*—Shape: Elliptic to broadly elliptic. Margin: Very slightly revolute, very short and finely serrate with approximately 30 teeth per cm. Apex: Apiculate. Base: Obtuse. Venation pattern: Pinnate. Length of mature leaf: Approximately 7.9 cm. Width of mature leaf: Approximately 3.4 cm. Texture of upper and lower surfaces: Smooth, glabrous. Color of upper surface of young foliage: Between 137A and 141A with venation of 147A tinged with 178A to 178B. Color of lower surface of young foliage: 137C to 138A with venation of 147B to 147C tinged with 178A to 178B. Color of upper surface of mature foliage: 137A with venation of 147A tinged with 178A to 178B. Color of lower surface of mature foliage: 137C with venation of 147B to 147C tinged with 178A to 178B.

*Petiole.*—Shape: V-shaped. Length: Approximately 3.0 mm. Width: Approximately 3.0 mm. Height: Approximately 3.0 mm. Color: upper side of 178B and lower side 147B to 147C.

Flowering description:

*Flowering habit.*—Freely flowering under outdoor growing conditions with substantially continuous blooming from summer through late summer.

*Lastingness of flower on the plant.*—Approximately 10 days.

*Lastingness as a cut flower.*—Approximately 10 days.

*Flowering response time.*—Approximately 60 days.

Inflorescence description:

*General description.*—Type: Compound terminal panicle, self-cleaning. Fragrance: Moderate, sweet and pleasant; typical *Phlox paniculata* scent. Height: Approximately 14.2 cm. Width: Approximately 12.3 cm. Quantity of opened flowers per inflorescence: Approximately 25. Rate of flower opening: Approximately 25% of the flowers at any stage.

*Peduncle.*—Strength: Strong. Aspect: Erect primary peduncles with secondary peduncles at approximately a 60° angle. Length of primary: Approximately 10.3 cm. Diameter of primary: Approximately 2.0 mm. Length of secondary: Approximately 2.5 cm. Diameter of secondary: Approximately 1.5 mm. Texture: Smooth, glabrous. Color: 146B to 146C flushed with N186C to 200B.

Flower description:

*General description.*—Type: Single. Shape: Salverform. Aspect: Upright to outward.

*Bud just before opening.*—Quantity per inflorescence: Approximately 75. Shape: Oblanceolate. Length: Approximately 2 cm. Diameter: Approximately 4.0 mm. Color: Petals of N57B with tube area of 59A to 187A; calyx N186C to 200A tinged with 147B to 147C at base. Rate of opening: Approximately 4 days.

*Corolla.*—Depth: Approximately 2.8 cm. Diameter: Approximately 3.2 cm.

*Petals.*—Quantity: 5, lower 55% of each petal fused into a narrow tube. Arrangement: Rotate. Appearance: Dull. Shape, lobe: Spathulate. Margin: Entire. Apex: Rounded. Length: Approximately 3.7 cm. Length of free portion: Approximately 1.6 cm. Width: Approximately 1.7 cm. Texture of upper and lower surfaces: Smooth. Color of upper surface when first open: 52A with N66A at tube opening; tube of N79C. Color of lower surface when first open: 55A with the tube of N80A. Color of upper surface when fully open: 52B with N57A to N66A at tube opening; tube of N80A. Color of lower surface when fully open: 55B to 55C with the tube of N79C. With age petal area fades to 51A.

*Calyx.*—Shape: Campanulate. Length: Approximately 9.0 mm. Diameter: Approximately 4.0 mm.

*Sepals.*—Quantity: 5, lower 66% fused into a narrow tube. Arrangement: In a single whorl. Appearance: Dull. Shape: Linear. Margin: Entire. Apex: Narrow apiculate. Length: Approximately 9.0 mm. Width: Approximately 3.0 mm. Texture of upper and lower surfaces: Smooth. Color of upper surface of immature sepals: N186C to 200A tinged with 147B to 147C at base. Color of lower surface of immature and mature sepals: 147B with tips flushed with N186C; 147D at base. Color of upper surface of mature sepals: 147A to 147B with tips flushed with N186C; 145A to 145B at base.

*Pedicel.*—Strength: Strong. Aspect: Erect when directly adjoining peduncle, others at an approximately 60° angle. Length: Approximately 7.0 mm. Diameter: Approximately 1.0 mm. Texture: Smooth, glabrous. Color: 144A to 146A.

*Reproductive organs.*—Androecium: Stamen quantity: 5 per flower, basifixed. Anther shape: Oblong. Anther length: Approximately 2.0 mm. Filament length: Approximately 1.0 mm. Anther color: 8D. Pollen amount: Low to moderate. Pollen color: 8B to 8C. Gynoecium: Pistil quantity: 1 per flower. Pistil length: Approximately 2.1 cm. Stigma shape: Cleft (3-parted). Stigma color: 150D. Style length: Approximately 1.9 cm. Style color: N77B. Ovary color: 143A.

Seed and fruit production: Neither seed nor fruit production has been observed.

Disease and pest resistance: Good mildew resistance. No particular resistance or susceptibility to other diseases or insects noted to date.

What is claimed is:

1. A new and distinct cultivar of *Phlox* plant named 'Tequila Sunrise', substantially as herein shown and described.

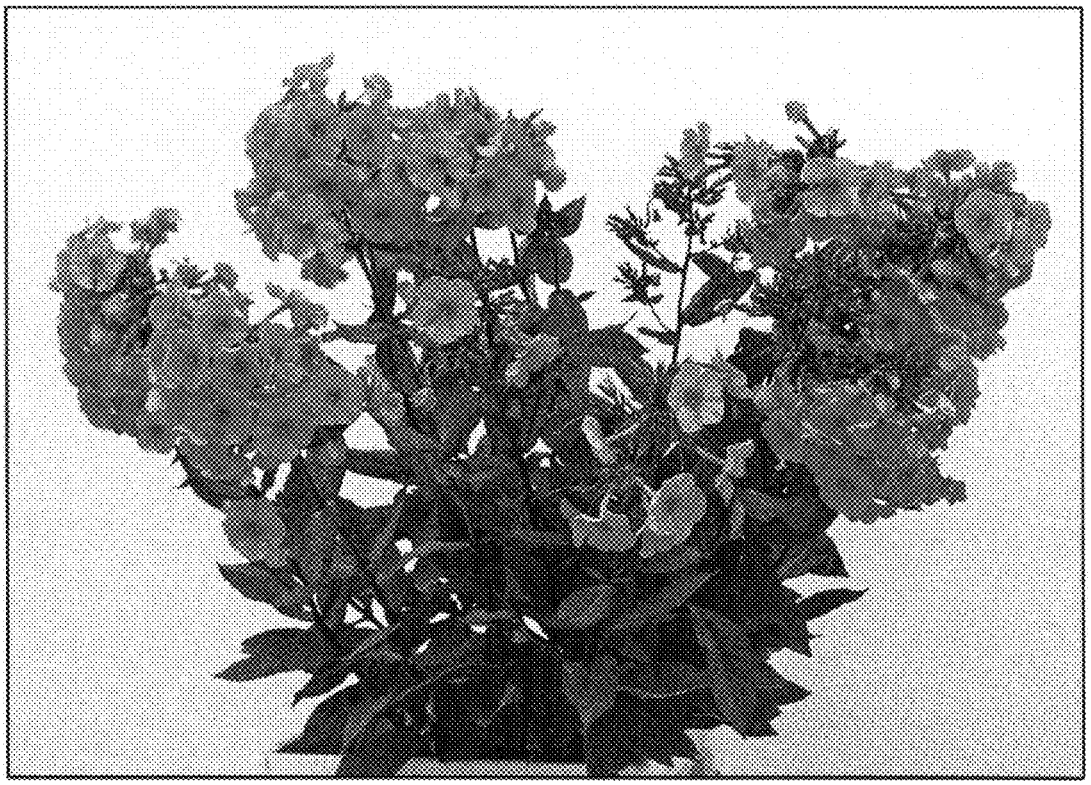

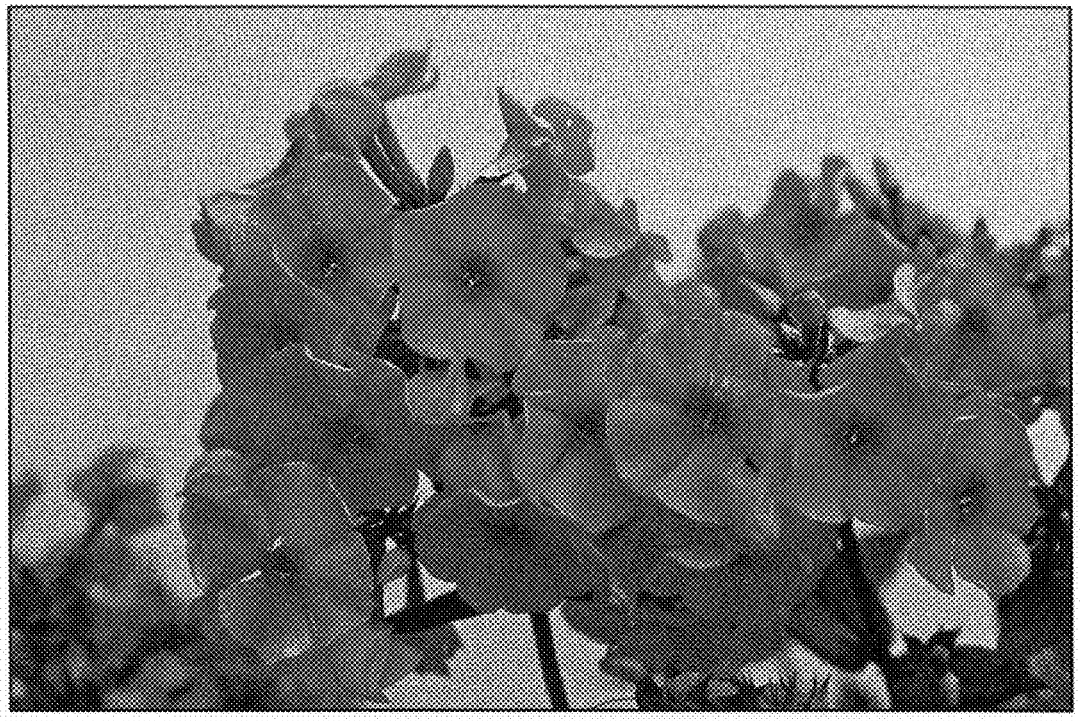
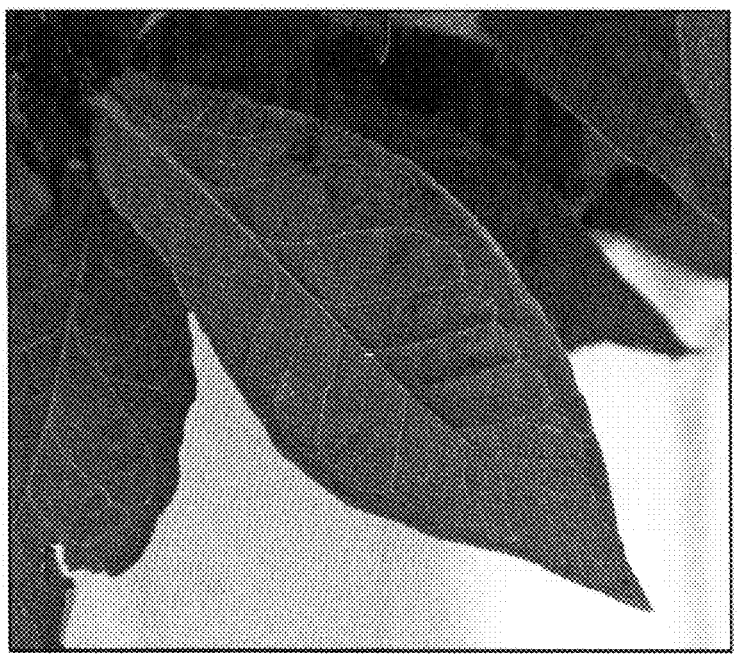

* * * * *